United States Patent
Curry et al.

(10) Patent No.: US 9,316,643 B2
(45) Date of Patent: Apr. 19, 2016

(54) SALIVARY DIAGNOSTIC SYSTEMS

(71) Applicant: Beam Technologies, LLC, Louisville, KY (US)

(72) Inventors: Alexander D. Curry, Louisville, KY (US); Alex X. Frommeyer, Louisville, KY (US); Daniel E. Dykes, Louisville, KY (US)

(73) Assignee: Beam Technologies, LLC, Louisville, KY (US)

( * ) Notice: Subject to any disclaimer, the term of this patent is extended or adjusted under 35 U.S.C. 154(b) by 0 days.

(21) Appl. No.: 14/188,006

(22) Filed: Feb. 24, 2014

(65) Prior Publication Data

US 2014/0242682 A1 Aug. 28, 2014

Related U.S. Application Data

(60) Provisional application No. 61/768,933, filed on Feb. 25, 2013.

(51) Int. Cl.

| | |
|---|---|
| *G01N 1/10* | (2006.01) |
| *G01N 9/30* | (2006.01) |
| *G01N 33/574* | (2006.01) |
| *G01N 33/53* | (2006.01) |
| *G01N 33/569* | (2006.01) |
| *G01N 1/00* | (2006.01) |
| *A61B 10/00* | (2006.01) |
| *B01L 3/00* | (2006.01) |
| *G01N 1/40* | (2006.01) |

(52) U.S. Cl.
CPC .......... *G01N 33/574* (2013.01); *A61B 10/0051* (2013.01); *B01L 3/00* (2013.01); *G01N 1/00* (2013.01); *G01N 33/5308* (2013.01); *G01N 33/56911* (2013.01); *G01N 33/56983* (2013.01); *G01N 2001/4088* (2013.01)

(58) Field of Classification Search
CPC ............ G01N 33/574; G01N 33/5308; G01N 33/56911; G01N 33/56983
USPC ........................ 422/68.1, 81, 82, 82.01–82.13
See application file for complete search history.

(56) References Cited

U.S. PATENT DOCUMENTS

| | | | |
|---|---|---|---|
| 2004/0086427 A1* | 5/2004 | Childers et al. | 422/100 |
| 2008/0176271 A1* | 7/2008 | Silver et al. | 435/29 |

OTHER PUBLICATIONS

Atkinson, Kelly R., et al. "Rapid saliva processing techniques for near real-time analysis of salivary steroids and protein." Journal of clinical laboratory analysis22.6 (2008): 395-402.*

* cited by examiner

*Primary Examiner* — Lyle Alexander
*Assistant Examiner* — Robert Eom
(74) *Attorney, Agent, or Firm* — Alexander D. Curry

(57) ABSTRACT

Salivary diagnostic systems are provided for improved disease diagnosis and overall health care. Salivary diagnostic systems are provided for the plurality of steps required in salivary diagnostic processes. The salivary diagnostic systems are interchangeably coupled by various methods and steps and include a collection system, a filter system, an evaluation system, and a reporting system. One or more salivary diagnostic systems are comprised in at least one salivary diagnostic device. Salivary diagnostic devices include a toothbrush, an implement, and a stand-alone system. The systems provide for the collection, filtration, and evaluation of saliva samples and the reporting of diagnostic data derived from the evaluation of saliva samples.

18 Claims, 4 Drawing Sheets

COLLECTION SYSTEM

FILTER SYSTEM

EVALUATION SYSTEM

REPORTING SYSTEM

SALIVARY DIAGNOSTIC SYSTEMS

CROSS-REFERENCE TO RELATED APPLICATIONS

This application claims priority to U.S. Provisional Applications No. 61/768,933 filed on Feb. 25, 2013.

BACKGROUND OF INVENTION

This invention relates to salivary diagnostics, particularly relating to systems and methods for salivary diagnostic testing. In particular, the invention relates to the collection, filtering, and evaluation of saliva samples for salivary diagnostic testing and the reporting of results of salivary diagnostic testing.

Humans have three major salivary glands that are the parotid, submandibular, and sublingual. Additionally, humans have minor salivary glands. Salivary glands secrete a rich mixture of biological chemicals, electrolytes, proteins, genetic material, polysaccharides, and other molecules. Most of the substances secreted by the salivary glands enter the salivary gland acinus and duct system from surrounding capillaries via the intervening tissue fluid. The level of each salivary component varies significantly depending on the health status of the individual and the presence of disease, both oral and systemic. The measurement of these components makes it possible to screen for a large array diseases, disorders, and conditions.

Current diagnostic methods include blood analysis, biopsy, and other large scale tests, which all cause considerable discomfort to the patient. Blood analysis requires the drawing of blood with the use of a hypodermic needle. Biopsy requires the removal of tissue from the suspected affected area. Current diagnostic methods also require significant amounts of time to obtain results with some tests taking multiple days or even weeks to complete. Often, this requires a patient to visit a doctor's office for the initial sample collection and again to obtain the results. Collection of samples often requires the expertise of a medical practitioner, which is costly. Evaluation of samples is often completed in a sophisticated laboratory, which is also very costly.

Consequently, medical practitioners and patients are in need of an adequate minimally invasive method of diagnosing diseases, disorders, and conditions. Moreover, medical practitioners and patients are in need of a quicker method of diagnosing diseases, disorders, and conditions. Further still, patients and the health care industry are in need of less expensive methods of diagnosing diseases, disorders, and conditions. The required expertise, specialized equipment, and general expense of diagnostics have made diagnostics an expensive and time consuming process. Consequently, a diagnostic process that does not require medical practitioner sample extraction, sophisticated laboratories, and long processing times is desirable for medical practitioners, patients, and the health care industry.

BRIEF SUMMARY OF THE INVENTION

The invention aims to provide a salivary diagnostic system for the diagnosis and detection of disease and disease risk characteristics. The salivary diagnostic system comprises a collection system, a filter system, an evaluation system, and a reporting system. Optionally, the salivary diagnostic system further comprises a waste system. These systems allow the salivary diagnostic system to collect saliva samples, filter said saliva samples, evaluate saliva samples for disease and disease risk characteristics, and report results of said evaluation.

The collection system collects the saliva sample and, often, stores the saliva sample in a reservoir until the sample is transferred to the filter system. The filter system is fluidly coupled to the collection system and filters the saliva sample to a form that is suitable for evaluation. The evaluation system is, often, fluidly coupled to the filter system and evaluates the saliva sample utilizing various methods to diagnosis and detect disease and disease risk characteristics. The evaluation system transmits the evaluated results to the reporting system, which provides the user with a medium to review the results of the evaluation. The waste system collects the byproduct of the saliva sample that is not used for evaluation.

Accordingly several advantages are to provide a salivary diagnostic system, to provide a noninvasive means for diagnosing and detecting disease and disease risk characteristics, to provide a collection means for saliva samples, to provide filtering for saliva samples prior to evaluation, to provide evaluation of saliva samples, to provide reporting of evaluated results of saliva samples, and to provide these functions in one or more coupled systems. Still further advantages will become apparent from a study of the following descriptions and the accompanying drawings.

DETAILED DESCRIPTION OF THE INVENTION

Figure 1:
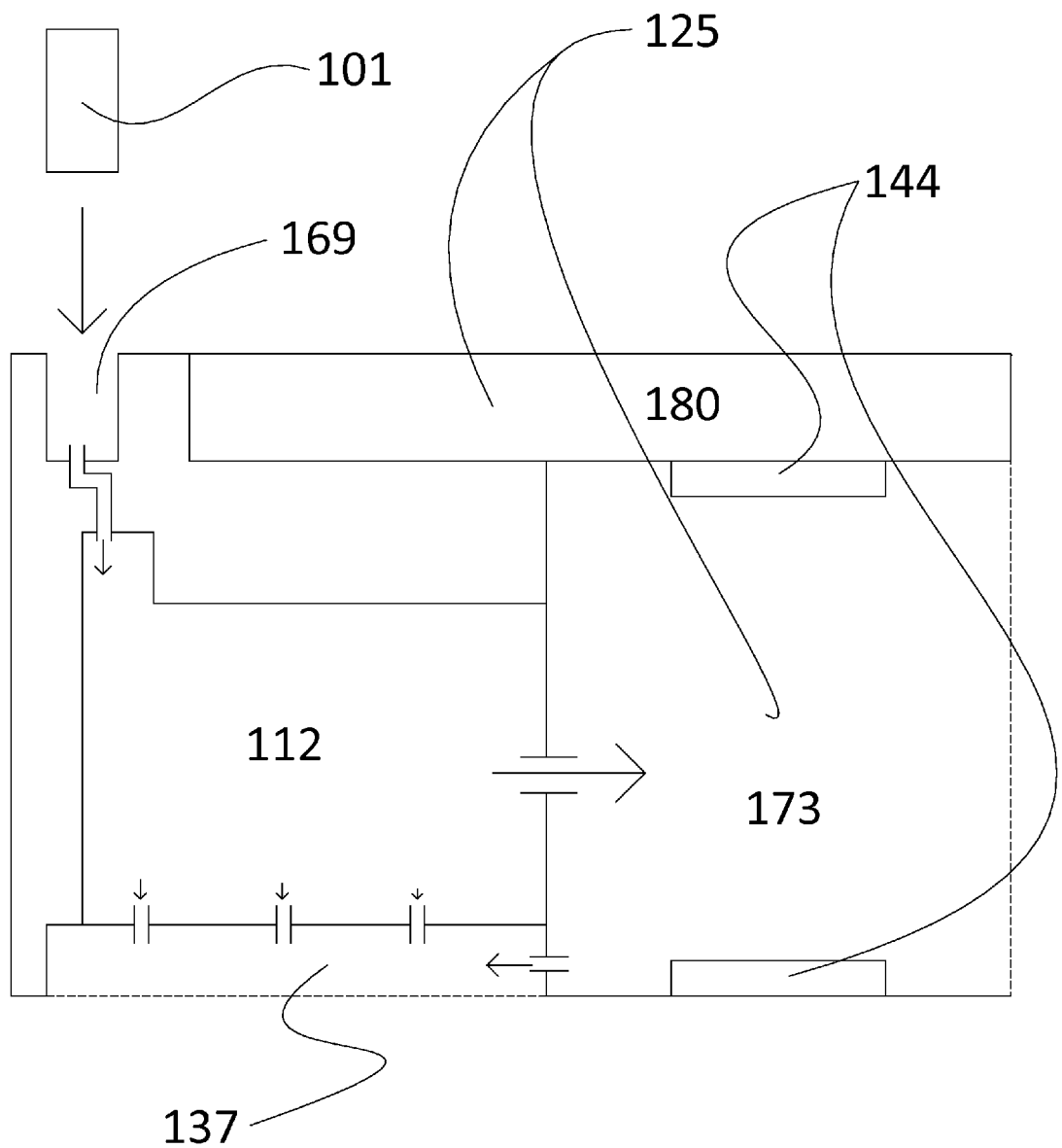
FIG. 1 is a schematic view of a salivary diagnostic system with a collection system, filter system, evaluation system, and waste system according to multiple embodiments and alternatives.

Salivary diagnostic systems are encompassed in a plurality of preferred embodiments that shall be discussed in the present section.

A plurality of embodiments comprises salivary diagnostic systems including a collection system, a filter system, an evaluation system, and a reporting system. The salivary diagnostic systems are interchangeably configured to be coupled by various methods and steps.

In some embodiments, a collection system is configured to collect at least one saliva sample from the oral cavity of a user for the detection and diagnosis of disease. Generally, the collection system collects a specified amount of saliva from a user comprising a saliva sample that is then used by various other salivary diagnostic systems. The specified amount of saliva is standardized in some instances, and varied in accordance with a specific test in other instances. The saliva sample obtained by the collection system is transferred to a filter system, an evaluation system, or both a filter system and an evaluation system, consecutively. Accordingly, a collection system comprises multiple embodiments of collection methods and associated structures.

In some embodiments, the collection system is at least one microfluidic channel and a reservoir, wherein at least one microfluidic channel is fluidly coupled to the reservoir. A microfluidic channel is characterized as having at least one solid side configured to create a depression in a solid surface such that the microfluidic channel can retain collected fluid; the fluid is, often, oral fluid. A microfluidic channel is further characterized as handling small fluid volumes, including volumes less than Pico liters, and providing an interface that exhibits the microscale behavior of fluids. Several methods of collecting fluid via a microfluidic channel exist including both passive and active fluid control techniques. One passive fluid control technique utilized for the collection of fluid via the microfluidic channel is capillary action. Several active fluid control techniques utilized for the collection of fluid via the microfluidic channel are rotary drives, micro pumps, and micro valves.

A microfluidic channel is further characterized by its typical size and the consequential effects on fluids. The diameter of a microfluidic channel typically ranges in size from about 100 nanometers to several hundred micrometers. Accordingly, this small size provides for atypical behavior of fluids. For example, the Reynolds number of a fluid is often lowered as a result of being drawn into a microfluidic channel. This affect allows for the manipulation of fluid different from the manipulation possible on the macro scale of fluids.

In operation, the microfluidic channel is fluidly coupled to the oral fluid contained in or expelled from the oral cavity of the user. The oral fluid is drawn into the microfluidic channel using either passive or active fluid control techniques. The oral fluid travels through the microfluidic channel and is transferred to the reservoir that is fluidly coupled to the microfluidic channel. Accordingly, several advantages are provided by utilizing a microfluidic channel for the collection system. A microfluidic channel provides for faster collection and analysis times due to shorter diffusion distances and high surface-to-volume ratios.

Additionally, a microfluidic channel is easily integrated into multiple structural embodiments. This integration allows for a plurality of oral fluid collection techniques to be utilized including drooling and pooling under the tongue. A microfluidic channel provides a versatile option for the collection system.

In some embodiments, the collection system is a capillary tube and a reservoir, wherein a capillary tube is fluidly coupled to a reservoir. A capillary tube uses capillary action to draw a fluid from a surface into the tube to be transported. Capillary action forces the fluid into the tube due to the combination of surface tension and adhesive forces between the fluid and the tube.

In operation, the capillary tube is fluidly coupled to the oral fluid contained in or expelled from the oral cavity of the user. Capillary action forces the oral fluid into the capillary tube that is fluidly coupled to a reservoir. The oral fluid flows through the capillary tube and enters a reservoir for storage. A capillary tube provides a practical embodiment of the collection system that is economical and easily manufacturable.

In some embodiments, the collection system is an absorptive material, a constriction mechanism, and a reservoir. An absorptive material is fluidly coupled to the oral fluid contained in or expelled from the oral cavity of a user. The fluid coupling allows for the process of absorption to move the oral fluid into the interstitial space of the absorptive material up to the point of saturation. Prior to or at the point of saturation, the constrictive mechanism applies force to the absorptive material, thus constricting the absorptive material. As the absorptive material is constricted, the oral fluid is expelled from the absorptive material into the fluidly coupled reservoir for storage.

Absorptive materials are chosen from the group tissue paper, cotton, sponge, fluff pulp, superabsorbent polymer (SAP), and any combination thereof. A constriction mechanism is a mechanical actuator that acts to constrict the absorptive material, thus expelling the fluid contained within it. For example, the constriction mechanism is a piston-cylinder configuration, wherein the absorptive material is positioned within the cylinder. The piston moves within the cylinder to compress and constrict the absorptive material, thus expelling its fluid. The fluid expelled from the absorptive material is transferred to a fluidly coupled reservoir for storage.

Optionally, the absorptive material collects oral fluid by having the user drool oral fluid onto the absorptive material, wherein the oral fluid is then absorbed and retained. Alternatively, oral fluid is pooled under the tongue of the user and the absorptive material is placed in the oral cavity. The absorptive material is fluidly coupled with the oral fluid, where it is absorbed and retained by the absorptive material. Further still, the oral fluid is collected by the absorptive material by fluidly coupling the two within the oral cavity without special preparation by the user. In other words, the oral fluid is collected without the user having to prepare the saliva for collection within his/her own oral cavity.

In some embodiments, the collection system is a pump fluidly coupled to a reservoir, wherein the pump transfers fluid to the reservoir. Various embodiments of pumps exist in the present invention. A pump of the collection system is chosen from the group gear pump, screw pump, rotary vane pump, plunger pump, diaphragm pump, piston displacement pump, radial piston pump, rotary lobe pump, progressive cavity pump, regenerative pump, peristaltic pump, pulser pump, centrifugal pump, radial-flow pump, axial-flow pump, mixed-flow pump, and valveless pump.

A gear pump is a rotary pump where fluid is pushed between two gears. Alternatively, a screw pump is a rotary pump where two screws turn against each other to pump the fluid. A rotary vane pump comprises a cylindrical rotor encased in similarly shaped housing, wherein the rotor turns and the vanes trap fluid between the rotor and casing, thus pumping the fluid. Optionally, a plunger pump comprises a reciprocating plunger that pushes the fluid through at least one open valve. Similarly, a diaphragm pump uses a plunger to pressurize hydraulic oil to flex a diaphragm in the pumping cylinder. Alternatively, a piston displacement pump reciprocates a high-pressure seal and piston to pump the fluid. A radial piston pump utilizes pistons extending in a radial direction symmetrically around a drive shaft forcing fluid movement. A rotary lobe pump uses two lobes that rotate and vary the pressure within the casing causing the fluid to flow through. Alternatively, a progressive cavity pump transfers fluid using the progress of a sequence of small, fixed-shape cavities as a rotor is turned. A regenerative pump comprises an impeller with a large number of radial blades, where the fluid is transferred between blades providing additional energy. A peristaltic pump comprises a flexible tube fitted inside a circular casing wherein a rotor compresses and decompresses the tube forcing the fluid to flow. A pulser pump has no moving parts and utilizes gravity to force fluid to flow upward. A centrifugal pump uses a rotating impeller to increase pressure and flow rate of a fluid. Optionally, a radial-flow pump operates by having fluid enter along the axial plane and accelerated by the impeller such that the fluid exits at right angles to the shaft. An axial-flow pump operates with the fluid entering and exiting along the same direction parallel to the shaft. Additionally, a mixed-flow pump functions as a mix between both radial-flow and axial-flow. Lastly, a valveless pump combines rotary and reciprocating motion to provide synchronized helical motion that allows for proper fluid flow without valves for the suction and discharge ports of the pump, thus the pump is valveless.

A pump is fluidly coupled using tubing or the like to the oral fluid contained in or expelled from the oral cavity of the user. The oral fluid is actively transferred through the pump to the fluidly coupled reservoir. The reservoir stores the oral fluid prior to filtering or evaluation.

In some embodiments, the collection system is disposable, wherein the collection system is disposed of following its use. Accordingly, a new collection system is used every time a saliva sample is collected. Alternatively, the collection system is reusable, wherein the collection system is sufficiently cleaned following its use. Accordingly, the same collection system is used to collect multiple saliva samples over a period of time.

In some embodiments, the reservoir of the collection system comprises a fluid level sensor that detects the level of the oral fluid transferred to the reservoir. The fluid level sensor further detects when the oral fluid level is at a specified level. Optionally, the specified level corresponds to a level sufficient for use with the salivary diagnostic system. Additionally, the fluid level sensor sends a signal indicating the specified level has been attained. Accordingly, this signal leads to cessation of oral fluid collection by physically stopping collection or signaling to a user to stop collection.

The fluid level sensor is chosen from the group displacement level gauge, load cell, magnetic level gauge, capacitance transmitter, magnetostrictive level transmitter, ultrasonic level transmitter, radar level transmitter, and any combination thereof.

A displacement level gauge comprises a column of solid material (a displacer) that is suspended in the reservoir. As the fluid volume in the reservoir increases, a buoyant force pushes up on the displacer. The displacer is calibrated to be displaced a certain distance when the fluid volume is at its specified level. The calibrated distance of the displacer causes it to exert a specified force on a force transducer. When the specified force is detected, the force transducer transmits a signal indicating the fluid has reached a specified level.

A load cell comprises at least one strain gauge affixed to the support structure of the reservoir such that distortions in the support structure are quantitatively measured. As the fluid volume increases, the force applied to and thus distortion exhibited by the support structure increases. When a specified amount of distortion that is correlated to a specified fluid volume is reached, the load cell transmits a signal indicating the fluid has reached a specified level.

A magnetic level gauge comprises a float that contains permanent magnets, which rides in an auxiliary column fluidly connected to the reservoir. As the fluid volume increases, the magnetic float rises within the auxiliary column. A magnetic switch is affixed to the auxiliary column at a specified point that correlates to a specified fluid volume. When the magnetic floater is detected by the magnetic switch, the magnetic switch transmits a signal indicating the fluid has reached a specified level.

A capacitance transmitter comprises either an insulated rod connected to a transmitter and the fluid, or an uninsulated rod attached to a transmitter and the reservoir wall. As the volume of fluid increases, the overall capacitance introduced by the rod increases proportionately. A capacitance bridge measures the capacitance of the rod and is calibrated to detect a specified capacitance that corresponds to a specified volume of fluid. When the specified capacitance is detected, the capacitance bridge and transmitter transmit a signal indicating the fluid has reached a specified level.

A magnetostrictive level transmitter comprises a sensor wire, piezoceramic sensor, transmitter, and magnetic float. The sensor wire runs through the center of the magnetic float and is attached to the piezoceramic sensor. The fluid level is detected by the transmitter sending a short current pulse down the sensor wire, which sets up a magnetic field along the length of the sensor wire. A timing circuit is also triggered on when the pulse is sent. The magnetic float reacts to the magnetic field and produces a torsional force in the sensor wire. The torsional force is detected by the piezoceramic sensor which sends out a varying electric signal dependent on the fluid level. A specified electric value corresponds to a specified fluid level, which indicates the fluid has reached a specified level.

An ultrasonic level transmitter comprises a transducer and timing circuit. The transducer transmits ultrasound to the surface of the fluid. The timing circuit measures the amount of time it takes the ultrasound wave to travel back to the transducer. The amount of time corresponds to fluid level of the reservoir. When a specified time that corresponds to a specified fluid level is detected, a signal is transmitted indicating the fluid has reached a specified level.

A radar level transmitter operates in the same manner as the ultrasonic level transmitter with exception of transmitting microwaves, which are reflected from the fluid surface. When a specified time that corresponds to a specified fluid level is detected, a signal is transmitted indicating the fluid has reached a specified level.

In some embodiments, the collection system does not comprise a reservoir and is instead fluidly coupled to a filter system. Accordingly, the oral fluid collected by the collection system is not stored in a reservoir but transferred directly to a fluidly coupled filter system.

In some embodiments, a filter system is configured to filter at least one saliva sample transferred from the collection system of the salivary diagnostic system for the detection and diagnosis of disease. Generally, the filter system filters the saliva sample such that the saliva sample exits the filter system in an optimum condition for evaluation. Optionally, the optimum condition for the saliva sample varies in accordance with the desired evaluation. However, in some embodiments, the optimum condition for the saliva sample is standardized such that desired evaluations are configured to use a standardized saliva sample provided by the filter system. Further still, in some embodiments, the optimum condition for the saliva sample provided by the filter system is, consequently, the optimum condition for a wide array of desired evaluations.

In some embodiments, the filter system is at least one inertial microfluidic filter. An inertial microfluidic filter comprises a rectangular channel cross-section optimized in size to filter specific sizes of particles, wherein variation of the size of the rectangular channel results in variation in the particle size filtered. The inlet of the rectangular channel provides a singular path for flow of the fluid and the particles to be filtered. Accordingly, the outlet of the rectangular channel comprises a four way junction, wherein the fluid and particles to be filtered enter the junction through a singular path consistent with the inlet. The remaining three flow paths of the four way junction radiate from the junction entrance at certain angular positions in relation to the junction entrance. In some embodiments, the remaining three flow paths radiate at 90° from the junction entrance, such that the remaining three flow paths are positioned at 90°, 180°, and 270° from the direction of flow of the junction entrance. In the present invention, the desired filtered fluid flows to the 180° channel such that the desired filtered fluid flows along a 180° or linear path through the four way junction. The filtered fluid then flows through additional filters within the filter system or is readied for the evaluation system. Additionally, the particles to be filtered flow to the 90° and 270° channels, which are perpendicular to the junction entrance. The particles are discarded after filtration.

An inertial microfluidic filter operates based on the principle that the particles are first subjected to drag forces in the channel which causes the particles to flow along the flow streamlines of the channel. Inertial lift forces cause the particles to laterally migrate across flow streamlines. The parabolic nature of the laminar flow exhibited by the particles produces a shear-induced inertial lift force that drives the particles away from the center of the channel to the walls. As the particles flow along the channel wall, the particles enter the four way junction. The particles continue to follow along the channel walls and continuously flow into the channels perpendicular to the junction entrance, therefore, being removed from the desired filtered fluid flow.

In some embodiments, the filter system is at least one microfluidic H-filter. A microfluidic H-filter comprises two inlet channels and an expanding outlet channel, often in the shape of a "V." Further, a microfluidic H-filter comprises a mixing channel between the two inlet channels and the outlet channel, such that the combination of all the channels resembles the letter "H." One inlet channel transports the fluid to be filtered; oral fluid in the present invention. The second inlet channel transports a collection buffer to be mixed with the fluid to be filtered. The mixing channel is optimized with respect to the diffusion coefficient of the fluid, the necessary contact time between the fluid and the buffer, and the geometry and dimensions of the mixing channel. The mixing of the buffer with fluid and the diffusion properties of both result in a purified sample of the desired fluid exhibited on one side of the outlet channel, such that the purified sample is extracted from the outlet channel on the corresponding side with the purified sample. If the Reynolds number is low, then an intervening membrane is not required. In some embodiments, a microfluidic H-filter is pump-driven such that a micro-pump facilitates the flow of fluids in the H-filter. Optionally, a microfluidic H-filter is made from paper and known has a paper H-filter, which does not require the use of a micro-pump to operate efficiently.

In some embodiments, the filter system is at least one weir, collectively a weir filter. In general, a weir filter comprises a channel for fluid flow and a flow barrier that allows a certain amount of fluid to pass over it. In some embodiments, the channel is comprised of at least two different levels, wherein the levels are separated by the flow barrier and the level after the flow barrier is lower than the level before the flow barrier. Accordingly, the fluid flows through the upper level of the channel into the flow barrier, wherein a portion of the fluid flows over the flow barrier and falls to the lower level of the channel. Additionally, the fluid flow that encounters the flow barrier, the fluid that does not flow over the flow barrier, is stopped and held by the flow barrier, often in a pool.

In some embodiments, the fluid flow that encounters the flow barrier is comprised of larger particulates, such the larger particulates travel to the bottom of the flow. Additionally, the larger particulates are not desirable for saliva diagnostic evaluation. Therefore, the collection of larger particulates by the flow barrier creates an oral fluid filter that allows only small particulate saliva to travel to the lower level of the channel. Optionally, in some embodiments, the flow barrier comprises a membrane that allows small particulates and the fluid to pass through, which allows for fluid to ultimately pass through to the lower level of the channel. In some embodiments, multiple levels are incorporated into the channel along with multiple flow barriers, wherein each level and flow barrier is optimized to filter certain size particulates from the fluid.

In some embodiments, the filter system is a thermal-centrifugal filter, wherein the saliva sample is frozen after being transferred from the collection system. After a specified period of time, the saliva sample is thawed with or without the aid of a heating system. Accordingly, the freezing and thawing process of filtering the saliva facilitates the separation of mucus, cellular debris, and food particles from the desired portion of the saliva sample. The thawed saliva sample is then centrifuged for a specified amount of time at a specific angular velocity. After being centrifuged, the saliva sample is adequately separated, wherein the desired saliva is on the top of the sample and the undesired substances at the bottom of the sample. Accordingly, the desired saliva is removed from the sample and is ready for evaluation by the evaluation system.

In some embodiments, a thermal-centrifugal filter comprises at least one cooling system, at least one heating system, and at least one centrifuge. In some embodiments, a cooling system and a heating system are comprised in a singular embodiment such that one system both cools and heats the saliva sample. Additionally, in some embodiments, the rotation of the centrifuge generates energy that is harnessed for use in the cooling system, heating system, or any combination thereof.

In some embodiments, the cooling system is at least one Peltier element comprising two sides that cover a plurality of thermocouples and two electrical wires connected to opposite sides of the Peltier element. A voltage is passed through the wires and thus across the thermocouples creating a temperature difference between the two sides. Accordingly, one side becomes cool and can be cooled below ambient temperature. The cool side of the Peltier element is applied to the saliva sample to cool it and ultimately bring it to a temperature below the freezing point, thus freezing the saliva sample.

In some embodiments, the cooling system of the thermal-centrifugal filter is a vapor-compression refrigeration system comprising a compressor, a condenser, an expansion valve, and an evaporator. The vapor-compression refrigeration system utilizes a refrigerant that travels through the components comprising the vapor-compression refrigeration system. The refrigerant operates as a liquid, a vapor, and a combination thereof. The liquid-vapor combination enters the evaporator of the vapor-compression refrigeration system and cools it significantly. A fan external to the evaporator blows air across the evaporator cooling the saliva sample. The temperature of the evaporator is optimized to allow for adequate cooling of the saliva sample below the freezing point, thus freezing the saliva sample.

In some embodiments, the heating system of the thermal-centrifugal filter is at least one Peltier element comprising two sides that cover a plurality of thermocouples and two electrical wires connected to opposite sides of the Peltier element. The Peltier element of the heating system operates in the same manner as the Peltier element of the cooling system. Accordingly, one side becomes cool and one side becomes warm when a voltage is applied. The warm side is applied to the saliva sample to begin the thawing process. The Peltier element warms the saliva sample beyond the freezing point, thus thawing the sample.

In some embodiments, the heating system of the thermal-centrifugal filter is at least one resistance wire, wherein electric current is input into the resistance wire and the resistance of the wire causes the resistance wire to heat up. Optionally, the resistance wire is made of Nichrome 80/20, which exhibits a high resistance. The heat generated by the resistance wire is applied to the frozen saliva sample to facilitate raising the temperature of the saliva sample above the freezing point, thus thawing the saliva sample.

In some embodiments, the heating system of the thermal-centrifugal filter is at least one vapor-compression heat pump comprising a compressor, a condenser, an evaporator, and an expansion valve. Refrigerant is transferred through the heat pump in the following order: the compressor, the condenser, the expansion valve, the evaporator, and back to the compressor to repeat the process. The refrigerant enters the condenser as a vapor, which is at a high temperature, and exits as a liquid. The heat removed from the refrigerant vapor is blown from the condenser to the frozen saliva sample. The warm air from the heat pump raises the temperature of the saliva sample above the freezing point, thus thawing the saliva sample.

A centrifuge puts the saliva sample in rotation around a fixed axis by applying a force perpendicular to the fixed axis. The rotation is actuated by an electric motor or the like. An electric motor converts electric current into mechanical rotation. Additionally, an electric motor provides for different angular velocities to be utilized with the use of a control system. A centrifuge operates using the sedimentation principle, wherein the centripetal acceleration forces denser substances to separate out along the radial direction and lighter objects tend to move in the opposite direction. Accordingly, the sample is housed in a tube like structure such that denser objects move to the bottom of the structure and the lighter objects move to the top of the structure. In saliva filtering, a centrifuge facilitates the process of separating unwanted particulates from desired saliva, wherein the particulates settle to the bottom of the tube like structure and the desired saliva rises to the top of the structure. Optionally, the tube like structure is fixed at an angle to facilitate easier movement of particulates within the sample.

In some embodiments, the thermal-centrifugal filter is miniaturized to allow for use with small samples of saliva. In a miniaturized thermal-centrifugal filter, the cooling system is sized and optimized to cool smaller saliva samples in a shorter amount of time. Additionally, the heating system and the cooling system are comprised in a singular embodiment such that one condition of the singular embodiment provides cooling and another condition of the singular embodiment provides heating. Further still, the centrifuge is miniaturized with the utilization of an optimized electric motor for the smaller saliva sample being filtered. Moreover, the tube like structure is sized for use with the smaller saliva sample.

In some embodiments, the thermal-centrifugal filter is contained in a singular system such that the cooling system, heating system, and centrifuge are all contained within an enclosed system. In some embodiments, the singular system thermal-centrifugal filter is sized to be readily operable on a tabletop in a consumer or laboratory setting. In some embodiments, the singular system thermal-centrifugal filter comprises automated steps, wherein the collected sample is transferred to the tube like structure of the centrifuge and frozen, thawed, and centrifuged without human interaction. Additionally, the singular system thermal-centrifugal filter is automated in the extraction of the desired saliva sample such that the desired saliva sample is extracted from the tube like structure and readied for evaluation without human interaction.

In some embodiments, the filter system is at least one membrane filter configured to block certain size particles. A membrane filter comprises an array of holes that allow particles to pass through that are smaller than a specified size. Consequently, the holes do not allow particles to pass through that are larger than the specified size, thus blocking the larger particles and effectively filtering the particles. Optionally, multiple membrane filters comprise the filter system, wherein each membrane filter is optimized to filter out a certain size particle such that passage through the multiple membrane filters effectively filters all sizes of unwanted particles.

In some embodiments, an evaluation system is configured to evaluate at least one saliva sample transferred from the collection system or filter system of the salivary diagnostic system for the detection and diagnosis of disease. In general, the evaluation system evaluates at least one saliva sample and provides a reportable assessment of the saliva sample in relation to the diagnosis and detection of disease and disease risk characteristics. A plurality of tests exists for the evaluation of saliva to diagnose and detect disease and disease risk characteristics. Common evaluation techniques are chosen from the group enzyme-linked immunosorbent assay (ELISA), polymerase chain reaction (PCR), high-resolution mass spectrometry (HRMS), heavy metal detection, fiber-optic-based detection, and any combination thereof. Accordingly, a plurality of diseases and conditions is detected and diagnosed using these common evaluation techniques. Some of these diseases and conditions are chosen from the group reproductive hormone irregularities, pancreatic cancer, breast cancer, oral cancer, human immunodeficiency virus, viral hepatitis, parasitic infection, Helicobacter pylori infection, periodontal disease, influenza, cardiovascular disease, dental caries, use of illicit drugs, and other cancers. Moreover, further diseases and conditions are being detected and diagnosed through saliva diagnostics.

Accordingly, the evaluation system provides a standardized system to perform a plurality of saliva tests using the saliva sample collected by the collection system and, often, filtered by the filter system. In the present invention, the evaluation system provides a platform for a plurality of saliva diagnostic tests such that the plurality of saliva diagnostic tests is performed by a singular evaluation system. The present invention of the evaluation system provides a standardized platform that allows for easy integration of saliva diagnostic tests.

In some embodiments, the evaluation system is a cartridge evaluation system comprising a console that is configured to couple to at least one cartridge for evaluation of a saliva sample, wherein a cartridge is configured to perform at least one saliva diagnostic test. Optionally, the saliva sample is transferred to the console from the collection system or filter system. The console is configured to couple to at least one cartridge, wherein a cartridge is retained by and fluidly coupled to the console. In operation, the console fluidly transfers the saliva sample to a cartridge where a saliva diagnostic test is performed by the cartridge in conjunction with the console. The console provides the necessary utilities to the cartridge to effectively perform the saliva diagnostic test. Additionally, the console is configured to determine the outcome of the test performed by the cartridge. In the case of test outcome being determined by a color change, the console comprises an optical sensor that determines outcome of the test. Accordingly, the console is configured to determine the outcome of the various saliva diagnostic tests conducted by the cartridges.

In some embodiments, a cartridge of the cartridge evaluation system is disposable, wherein a cartridge is a single-use product and is disposed after use. Optionally, a cartridge is arranged to be electronically coupled to the console such that the cartridge and the console are in analog and/or digital communication. The electronic coupling of the cartridge and the console provides for communication chosen from the group identification of the test the cartridge performs, progress of testing, results of testing, saliva sample data, and any combination thereof.

In some embodiments, the evaluation system comprises at least one data transfer medium plug-in system, wherein the evaluation system is configured to be a plug-in to a data transfer medium, such as a mobile communication device, such that the plug-in utilizes the computing power of the data transfer medium and data is communicated between the two. Optionally, the plug-in operates in the same manner as the cartridge evaluation system described above but utilizes the computing power and convenience of the mobile communication device. Accordingly, a different cartridge is used for different tests and plug-in in conjunction with the mobile communication device acts as the console. In the present invention, the features of the mobile communication device are utilized for the evaluation of the saliva sample.

Alternatively, the plug-in comprises all of the necessary components to complete a certain saliva diagnostic test, wherein a separate plug-in is used for each saliva diagnostic test. Accordingly, the plug-in is removed from the mobile communication device after a test is completed and replaced with a different plug-in to conduct a different test.

In some embodiments, especially those where an observed chromatic change is evaluated, the evaluation system comprises a mobile communication device equipped with at least one image capturing device, such as a CMOS sensor. The mobile communication device along with a native software application is able to detect the saliva sample and evaluate the results of the test, which may be a chromatic change due to a certain chemical reaction.

In some embodiments, the evaluation system comprises a plurality of specified tests that are built into the system such that the utilities necessary to complete a plurality of tests are comprised in the evaluation system. Accordingly, the present embodiment does not require the use of interchangeable and/or disposable cartridges to perform different tests. Optionally, the evaluation system is partitioned such that different tests are performed within the same system. Additionally, the evaluation system is partitioned in such a way that multiple tests are performed concurrently. Accordingly, the saliva sample is transferred from the collection system or filter system and the evaluation system performs specified saliva diagnostic tests without human interaction, thus providing an automated evaluation system.

In some embodiments, the evaluation system is external to the other systems that comprise the saliva diagnostic system. Accordingly, the saliva sample is received from the collection system or filter system and transferred to the evaluation system using human interaction. The test is conducted by the evaluation system at different site from the collection and/or filtering of the saliva sample. For example, the saliva sample is collected and filtered in the home of the patient, and it is delivered to a laboratory where it is evaluated.

In some embodiments, the evaluation system comprises a transmitter that transmits results of tests performed by the evaluation system. The transmitter is chosen from the group universal serial bus (USB), serial port, wired Ethernet port, radio frequency, microwave communication, infrared short-range communication, near field communication, and short-range wireless communication via short-wavelength ultra-high frequency radio waves such as Bluetooth®.

In some embodiments, a waste system is configured to collect and store undesired portions of saliva and saliva that has been evaluated. A waste system is fluidly coupled to a collection system, filter system, and/or evaluation system, wherein the undesired portion or used saliva is fluidly transferred to the waste system for storage. In some embodiments, a waste system is reusable, wherein the contents of the waste system are easily emptied from the waste system. Additionally, the waste system is easily cleansed to provide renewed sanitary conditions to the waste system. Alternatively, a waste system is disposable, wherein the entire waste system is disposed of following a specified amount of use. Accordingly, the disposable waste system must be replaced with a new disposable waste system for continued use.

In some embodiments, at least one of the systems chosen from the group collection system, filter system, evaluation system, and any combination thereof is comprised in a toothbrush. Optionally, the toothbrush comprises a collection system such that the user collects the saliva sample with the toothbrush used daily. Alternatively, the toothbrush comprises both a collection system and a filter system, wherein the user's toothbrush collects a saliva sample and filters said saliva sample such that the saliva sample is readied for evaluation within the toothbrush. In the toothbrush comprising a collection system and a filter system, the toothbrush is fluidly coupled to an evaluation system to transfer the saliva sample. Alternatively, the toothbrush comprises a collection system, filter system, and an evaluation system, wherein the user's toothbrush collects a saliva sample, filters said saliva sample, and evaluates the saliva sample for the diagnosis and detection of disease and risk characteristics of disease.

In some embodiments, at least one of the systems chosen from the group collection system, filter system, evaluation system, and any combination thereof is comprised in a dental implement. Optionally, the dental implement comprises a collection system, wherein the dental implement is used to collect a saliva sample by at least one of the collection methods described herein. Alternatively, the dental implement comprises both a collection and a filter system, wherein the dental implement is used to collect a saliva sample and filter said saliva sample. Additionally, the dental implement comprising a collection system and a filter system fluidly couples to an evaluation system to transfer the saliva sample for evaluation. Alternatively, the dental implement comprises a collection system, a filter system, and an evaluation system, wherein the dental implement collects a saliva sample, filters said saliva sample, and evaluates the saliva sample for the diagnosis and detection of disease and risk characteristics of disease.

In some embodiments, at least one of the systems chosen from the group collection system, filter system, evaluation system, and any combination thereof is comprised in a mobile communication device plug-in. Optionally, the mobile communication device plug-in comprises a collection system, a filter system, and an evaluation system, wherein the mobile device plug-in collects a saliva sample, filters said saliva sample, and evaluates the saliva sample for the diagnosis and detection of disease and risk characteristics of disease with the aide of the mobile communication device.

In some embodiments, at least one of the systems chosen from the group collection system, filter system, evaluation system, and any combination thereof is comprised in a stand-alone system. Accordingly, the stand-alone system is only used for the purpose of saliva diagnostic testing. Optionally, the stand-alone system comprises a collection system, wherein the stand-alone system is used to collect a saliva sample. Alternatively, the stand-alone system comprises both a collection system and a filter system, wherein the stand-alone system collects a saliva sample and filters said saliva sample. Alternatively, the stand-alone system comprises a collection system, a filter system, and an evaluation system, wherein the stand-alone system collects a saliva sample, filters said saliva sample, and evaluates the saliva sample for the diagnosis and detection of disease and risk characteristics of disease.

In some embodiments, a reporting system is configured to report the results of the saliva diagnostic tests performed by an evaluation system. In general, the reporting system reports, processes, and stores the results of testing performed by the evaluation system. The reporting system utilizes data transfer mediums and network storage devices to effectively process, store, and report results of test completed by the evaluation system.

In some embodiments, the reporting system comprises a data transfer medium that comprises a receiver and a data processing unit. Accordingly, the data processing unit is chosen from the group microprocessor, microcontroller, field programmable gate array (FPGA), digital signal processing unit (DSP), application specific integrated circuit (ASIC), programmable logic, and combinations thereof.

Additionally, in some embodiments, the collector of the data processing unit is an electrically conductive wire, wherein the electrically conductive wire receives the electrical output of the receiver of the data transfer medium, such that the electrical output of the receiver of the data transfer medium is indicative of the results provided by the evaluation system.

Moreover, in some embodiments, the storage medium of the data processing unit is comprised of volatile memory and non-volatile memory, wherein volatile memory is used for short-term storage and processing, and non-volatile memory is used for long-term storage. Accordingly, in some embodiments, volatile memory is chosen from the group random-access memory (RAM), dynamic random-access memory (DRAM), double data rate synchronous dynamic random-access memory (DDR SDRAM), static random-access memory (SRAM), thyristor random-access memory (T-RAM), zero-capacitor random-access memory (Z-RAM), and twin transistor random-access memory (TTRAM). Optionally, in some embodiments, non-volatile memory is chosen from the group read-only memory (ROM), programmable read-only memory (PROM), erasable programmable read-only memory (EPROM), electrically erasable programmable read-only memory (EEPROM), flash memory, ferroelectric random-access memory (FeRAM), magnetoresistive random-access memory (MRAM), phase-change memory (PRAM), conductive-bridging random-access memory (CBRAM), silicon-oxide-nitride-oxide-silicon memory (SONOS), resistive random-access memory (RRAM), racetrack memory, nano-random-access memory (NRAM), and Millipede memory.

Further still, in some embodiments, the processor of the data processing unit is chosen from the group microprocessor and microcontroller.

Additionally, in some embodiments, the receiver of the data transfer medium is chosen from the group universal serial bus (USB), serial port, wired Ethernet port, radio frequency, microwave communication, infrared short-range communication, near field communication, and Bluetooth®. The receiver of the data transfer medium receives the results from tests performed by the evaluation system.

In some embodiments, the data transfer medium is a personal computer system, which is any general-purpose computer with a size and capability conducive to direct operation by an end-user. Optionally, the data transfer medium is a dental office computer system, which is any computer primarily used in a dental office for dental care purposes. Optionally, in some embodiments, the data transfer medium is a tablet personal computer, wherein the display medium and user input medium are comprised in a singular flat touch screen, and the tablet personal computer is a complete mobile computing system.

Optionally, in some embodiments, the data transfer medium is a mobile communication device capable of receiving and transmitting telephone calls. Optionally, in some embodiments, the data transfer medium is a dedicated system utilized only for the purposes set out for the data transfer medium. Optionally, in some embodiments, the data transfer medium is a television. Additionally, in some embodiments, the data transfer medium is an external charging station that replenishes the electrical energy of the power source of an implement.

Optionally, in some embodiments, the data transfer medium is a network router that forwards data packets between telecommunications networks, e.g. between the Internet and a personal computer. Optionally, in some embodiments, the data transfer medium is a web-enabled network storage device that is connected to the internet and acts as a database, commonly referred to as the "Cloud."

In some embodiments, the data transfer medium further comprises a transmitter. Optionally, the transmitter of the data transfer medium is chosen from the group universal serial bus (USB), serial port, wired Ethernet port, radio frequency, microwave communication, infrared short-range communication, near field communication, and Bluetooth®.

In some embodiments, the data transfer medium further comprises a display, wherein the display converts signals into a user-readable format. The user-readable format is characterized as a format that allows a user to easily determine the measurement from the display device.

In some embodiments, the data transfer medium further comprises a user interface. The user interface, in some embodiments, is embodied in the display such that the user interface can be viewed and manipulated using the display. Optionally, the user interface is manipulated through at least one medium external to the display. Alternatively, the user interface is manipulated using the display and at least one medium external to the display.

In some embodiments, the reporting system further comprises a network storage device, wherein the network storage device receives, stores, processes, and transmits results provided by the evaluation system. The network storage device is more commonly referred to, in some instances, as a network connected server. Additionally, in some instances, the network storage device is more commonly referred to as a "Cloud" server, wherein the storage space on the server is paid for as a service.

In some embodiments, the network storage device is connected to a network, wherein the network is chosen from the group Internet or intranet such that an intranet is a network managed and accessed by an internal organization and is not accessible to the outside world. The network is utilized by the network storage device for receiving and transmitting data. The mode for receiving and transmitting data through the network is chosen from the group universal serial bus (USB), serial port, wired Ethernet port, radio frequency, microwave communication, infrared short-range communication, near field communication, and Bluetooth®.

Additionally, in some embodiments, the network storage device processes data using at least one microprocessor, at least one microcontroller, or a combination thereof. The storage of data, in some embodiments, is comprised of volatile memory and non-volatile memory, wherein volatile memory is used for short-term storage and processing, and non-volatile memory is used for long-term storage. Accordingly, in some embodiments, volatile memory is chosen from the group random-access memory (RAM), dynamic random-access memory (DRAM), double data rate synchronous dynamic random-access memory (DDR SDRAM), static random-access memory (SRAM), thyristor random-access memory (T-RAM), zero-capacitor random-access memory (Z-RAM), and twin transistor random-access memory (TTRAM). Optionally, in some embodiments, non-volatile memory is chosen from the group read-only memory (ROM), programmable read-only memory (PROM), erasable programmable read-only memory (EPROM), electrically erasable programmable read-only memory (EEPROM), flash memory, ferroelectric random-access memory (FeRAM), magnetoresistive random-access memory (MRAM), phase-change memory (PRAM), conductive-bridging random-access memory (CBRAM), silicon-oxide-nitride-oxide-silicon memory (SONOS), resistive random-access memory (RRAM), racetrack memory, nano-random-access memory (NRAM), and Millipede memory.

The network storage device, optionally, is a network server primarily used for storing and processing data. Optionally, the network storage device is comprised of more than one network server such that the network servers operate in conjunction to increase the storing and processing capabilities of the network storage device. In some embodiments, the network storage device is provided as a service such that it is physically located at a location separate from the user, and the service provided is the storing and processing of data. In such embodiments, the network storage device is sometimes referred to as the "Cloud."

Referring to FIG. 1, a salivary diagnostic system is shown comprising four main systems, which are the collection system 101, filter system 112, waste system 137, and evaluation system 125. The collection system 101 collects a saliva sample from the user and is, often, separate from the remainder of the salivary diagnostic system during collection. The collection system 101 utilizes a collection method chosen from the group consisting of a microfluidic channel, capillary tube, absorptive material/constrictive mechanism, pump (micropump), and any combination thereof. Additionally, all or some of the components of the collection system 101 are disposable, wherein the disposable components are disposed of following a single use. Alternatively, all or some of the components of the collection system 101 are reusable, wherein the reusable components are cleaned and reused for more than one use. Additionally, some embodiments of the collection system 101 comprise and integrated filter that begins the filtration process prior to the saliva sample entering the filter system 112.

Still referring to FIG. 1, the collection system 101 is introduced to the remainder of the salivary diagnostic system by being detachably placed in the collection system coupler 169. When placed in the collection system coupler 169, the collection system 101 is fluidly coupled to the filter system 112, as indicated in FIG. 1. The saliva sample enters the filter system 112 where the desired portion of the saliva sample is filtered out of the saliva sample. The filter system 112 utilizes a filtration method chosen from the group consisting of inertial microfluidic filter, microfluidic H-filter, weir filter, thermal-centrifugal filter, membrane filter, and any combination thereof. The desired portion of the saliva sample is subsequently transferred to the fluidly coupled evaluation chamber 173. The undesired portion of the saliva sample is transferred to the fluidly coupled waste system 137, wherein it is stored for disposal. The waste system 137 is detachably connected to the salivary diagnostic system such that it can be detached for cleaning, as indicated by the dashed line shown in FIG. 1.

As shown in FIG. 1, the evaluation system 125 comprises an evaluation chamber 173 and a data processing unit/transceiver 180. The evaluation chamber 173 receives at least one test cartridge through a portion of the chamber that opens, as indicated by the dashed line. The desired portion of the saliva sample from the filter system 112 is fluidly transferred to the test cartridge in the evaluation chamber 173. The evaluation utilities 144 in the evaluation chamber 173 determine the results of the test performed in the test cartridge. The data processing unit/transceiver 180 process, store, and transmit the test results to a reporting system. Additionally, in some embodiments, the used saliva sample is transferred from the evaluation chamber 173 to the waste system 137.

Figure 2:
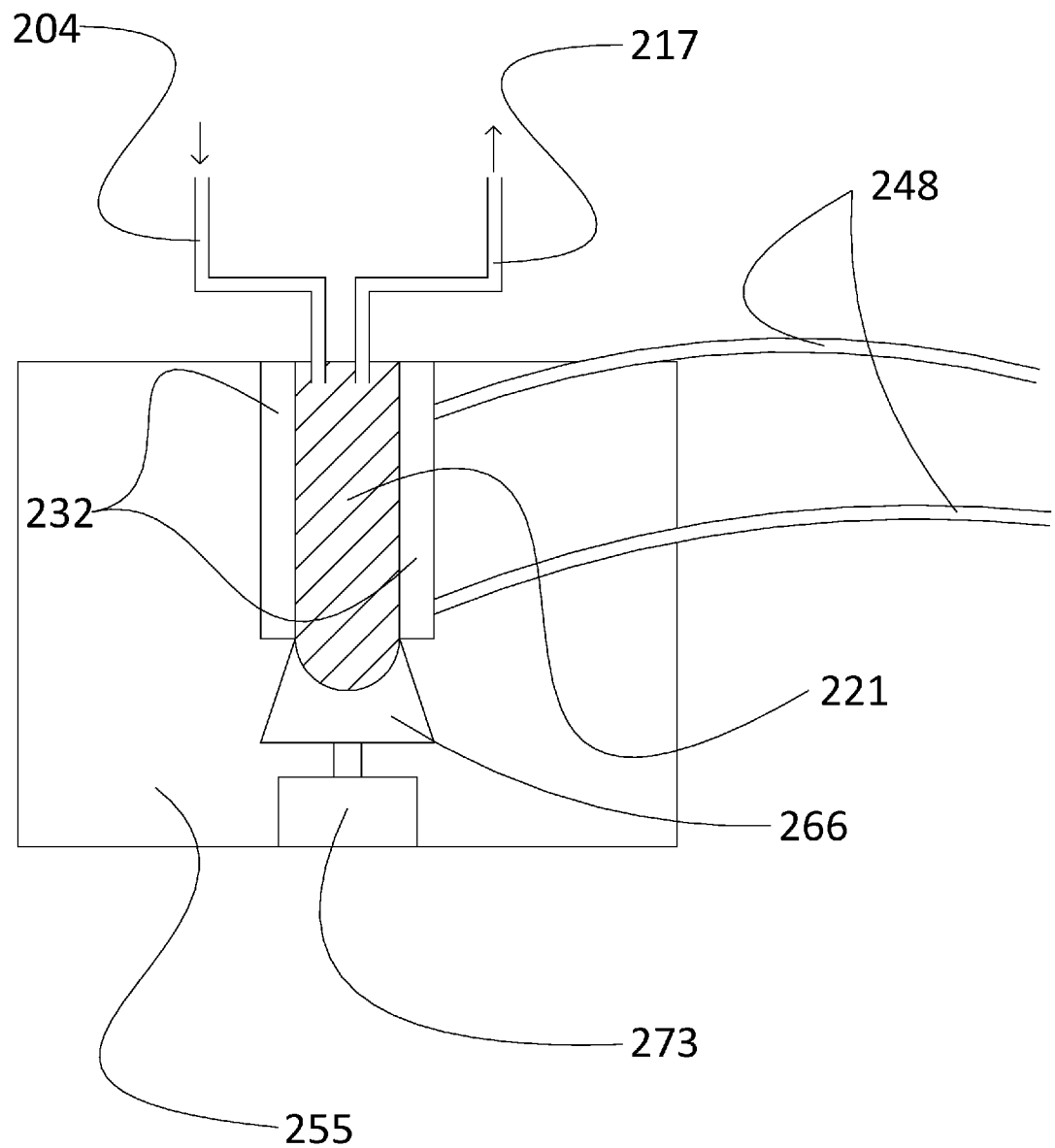
FIG. 2 is a schematic view of a thermal-centrifugal filter where the heating system, cooling system, and centrifuge are integrated according to multiple embodiments and alternatives.

Referring to FIG. 2, a thermal-centrifugal filter is shown comprising a centrifuge 255, at least one Peltier element 232, and a tube-like structure 221. A salvia sample travels through the inlet 204 from the collection system and enters the tube-like structure 221, where it is housed for the duration of the filtering process. The Peltier element 232 is cooled as current is passed through the Peltier lead wires 248. The cooling of the Peltier element 232 cools the tube-like structure 221, thus cooling the saliva sample until frozen. After a specified period of time, the current flow is reversed in the Peltier lead wires 248 forcing the Peltier element 232 to heat. The heat from the Peltier element 232 heats the tube-like structure 221 causing the saliva sample to thaw. The tube-like structure 221 is then rotated at a high angular velocity by the rotor 266 that is coupled to the electric motor 273, both of which are comprised in the centrifuge 255. Following the completion of centrifuging, the desired portion of the saliva sample has settled towards the top of the tube-like structure 221, and the undesired portion of the saliva sample has settled towards the bottom of the tube-like structure 221. The desired portion of the saliva sample is directed through the outlet 217 to the evaluation system for testing.

Figure 3:
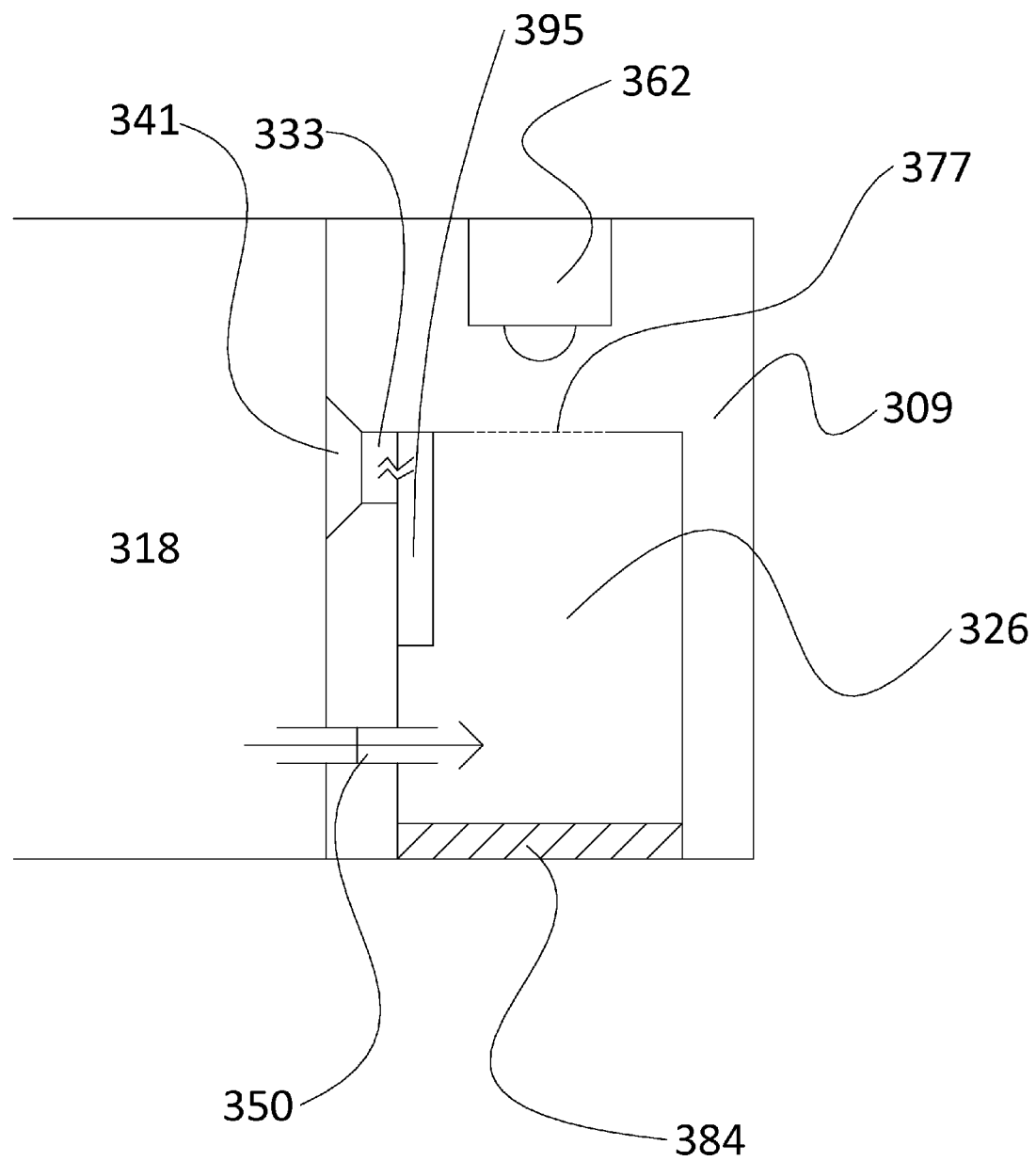
FIG. 3 is a schematic view of a cartridge evaluation system with a cartridge located in the evaluation chamber according to multiple embodiments and alternatives.
Figure 4:
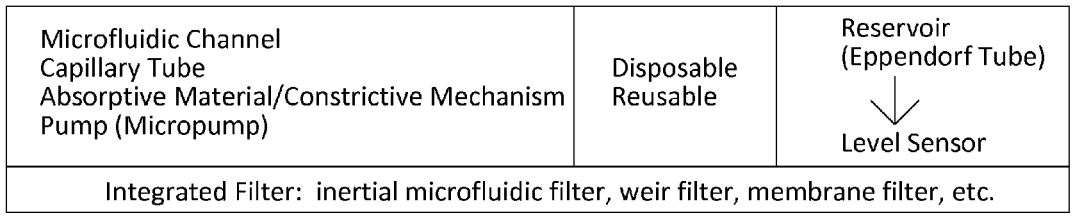
FIG. 4 is a flow diagram of possible embodiments for the collection system, filter system, evaluation system, and reporting system according to multiple embodiments and alternatives.
Figure 4:
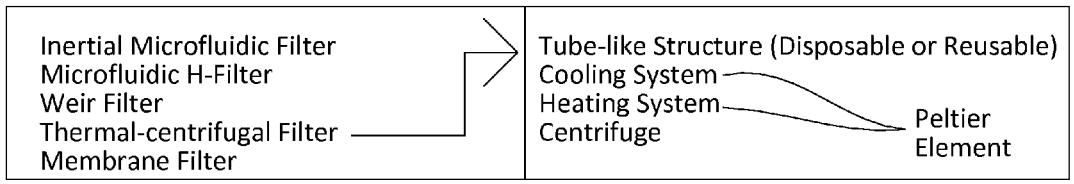
Figure 4:
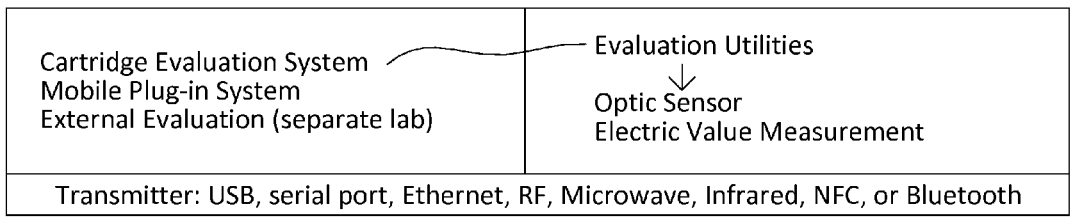
Figure 4:
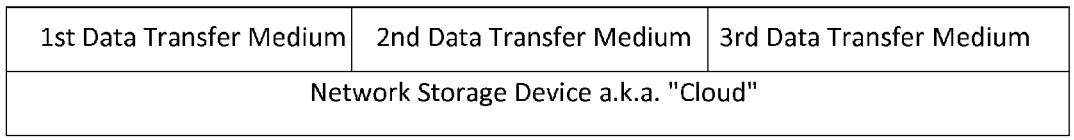

Referring to FIG. 3, a cartridge evaluation system is shown comprising a cartridge 326, an evaluation chamber 309, and evaluation utilities 362. The cartridge 326 is inserted into the evaluation chamber 309, wherein the cartridge electric contact 333 connects to the chamber electric contact 341. The cartridge electric contact 333 is electrically coupled to cartridge data processing unit 395 and identifies the cartridge 326 via the connection to the chamber electric contact 341. The cartridge 326 is fluidly coupled to the filter system 318 via the fluid coupler 350. The saliva sample travels into the cartridge 326 and contacts the immunoassay 384. The immunoassay 384 performs the salivary diagnostic test and exhibits a change to demonstrate the result of the test. The evaluation utilities 362 are provided access by the cartridge window 377 to the change exhibited by the immunoassay 384. The evaluation utilities 362 determine the result of the test and the transmitter transmits the results to the reporting system. The cartridge 326 is disposable and is accordingly discarded following the completion of the test. The cartridge 326 may be stored for further evaluation following the test. Alternatively, the evaluation utilities 362 may be comprised in an external mobile communication device, such that the built-in resources of the mobile communication device are utilized to evaluate the immunoassay 384, such as the digital camera comprised in the mobile communication device.

It will be understood that the embodiments described herein are not limited in their application to the details of the teachings and descriptions set forth, or as illustrated in the accompanying figures. Rather, it will be understood that saliva diagnostic systems, as taught and described according to multiple embodiments disclosed herein, are capable of other embodiments and of being practiced or carried out in various ways.

Also, it is to be understood that the phraseology and terminology used herein is for the purpose of description and should not be regarded as limiting. The use herein of "including," "comprising," "e.g.," "containing," or "having," and variations of those words is meant to encompass the items listed thereafter, and equivalents of those, as well as additional items.

Accordingly, the descriptions herein are not intended to be exhaustive, nor are they meant to limit the understanding of the embodiments to the precise forms disclosed. It will be understood by those having ordinary skill in the art that modifications and variations of these embodiments are reasonably possible in light of the above teachings and descriptions.

What is claimed is:

1. A salivary diagnostic system, comprising: a collection system configured to collect at least one saliva sample; a thermal-centrifugal filter configured to treat the at least one saliva sample; and an evaluation system configured to analyze the at least one saliva sample to detect and/or diagnose a disease or a disease risk characteristic; wherein the thermal-centrifugal filter and the evaluation system are enclosed within a single unit; and wherein the collection system is configured to detachably couple to the thermal-centrifugal filter.

2. The salivary diagnostic system of claim 1, wherein the collection system is selected from the group consisting of at least one microfluidic channel, a capillary tube, an absorptive material and constriction mechanism, a pump, and any combination thereof.

3. The salivary diagnostic system of claim 1, wherein the collection system further comprises at least one reservoir.

4. The salivary diagnostic system of claim 3, wherein the reservoir of the collection system further comprises at least one fluid level sensor selected from the group consisting of a displacement level gauge, load cell, magnetic level gauge, capacitance transmitter, magnetostrictive level transmitter, ultrasonic level transmitter, radar level transmitter, and any combination thereof.

5. The salivary diagnostic system of claim 1, wherein the collection system is fluidly coupled to the thermal-centrifugal filter.

6. The salivary diagnostic system of claim 1, wherein the thermal-centrifugal filter is housed in a sub-enclosure in the single unit.

7. The salivary diagnostic system of claim 1, wherein the evaluation system further comprises at least one evaluation technique selected from the group consisting of an enzyme-linked immunosorbent assay (ELISA), polymerase chain reaction (PCR), high-resolution mass spectrometry (HRMS), heavy metal detection, fiber-optic-based detection, and any combination thereof.

8. The salivary diagnostic system of claim 1, wherein the evaluation system is configured to provide a standardized platform for saliva diagnostic tests.

9. The salivary diagnostic system of claim 1, wherein the evaluation system is a cartridge evaluation system comprising a console that is configured to couple to at least one cartridge, wherein a cartridge is configured to perform at least one saliva diagnostic test.

10. The salivary diagnostic system of claim 1, wherein the evaluation system further comprises a data transfer medium with at least one image capturing device.

11. The salivary diagnostic system of claim 10, wherein the evaluation system is at least one data transfer medium plug-in system that is configured to communicate with the data transfer medium.

12. The salivary diagnostic system of claim 1, wherein the evaluation system further comprises utilities required by a plurality of saliva diagnostic tests.

13. The salivary diagnostic system of claim 1, wherein the evaluation system further comprises a transceiver that is configured to transmit and receive data indicative of saliva diagnostic tests.

14. The salivary diagnostic system of claim 13, wherein the transceiver of the evaluation system is selected from the group consisting of universal serial bus (USB), serial port, wired Ethernet port, radio frequency, microwave communication, infrared short-range communication, near field communication, Wi-Fi, short-range wireless communication via short-wavelength ultra-high frequency radio waves, and any combination thereof.

15. The salivary diagnostic system of claim 1, wherein at least one system of the salivary diagnostic system is comprised in a device chosen from the group consisting of a toothbrush, dental implement, data transfer medium plug-in, stand-alone system, and any combination thereof.

16. The salivary diagnostic system of claim 1, further comprising a reporting system that is configured to report results of saliva diagnostic tests.

17. The salivary diagnostic system of claim 16, wherein the reporting system further comprises a cloud computing network having at least one data processing unit that is configured to store and process data and a transceiver that is configured to receive and transmit data.

18. The salivary diagnostic system of claim 16, wherein the reporting system further comprises a data transfer medium having a transceiver that is configured to receive and transmit data, a data processing unit that is configured to store and process data.

* * * * *